(12) United States Patent
Liu et al.

(10) Patent No.: US 6,841,190 B2
(45) Date of Patent: Jan. 11, 2005

(54) ANTISOILING HARDCOAT

(75) Inventors: Junkang J. Liu, Woodbury, MN (US);
Bettie C. Fong, Woodbury, MN (US);
Bruce D. Kluge, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/690,425

(22) Filed: Oct. 21, 2003

(65) Prior Publication Data

US 2004/0081764 A1 Apr. 29, 2004

Related U.S. Application Data

(60) Division of application No. 09/923,749, filed on Aug. 7, 2001, now Pat. No. 6,660,388, which is a continuation-in-part of application No. 09/633,835, filed on Aug. 7, 2000, now Pat. No. 6,589,650.

(51) Int. Cl.[7] .................................................. B05D 5/06
(52) U.S. Cl. ...................... 427/64; 427/164; 427/365; 427/376.2; 427/385.5; 427/407.1; 427/419.2
(58) Field of Search .................. 427/64, 162, 164, 427/376.2, 376.1, 419.2, 207.1, 402, 289, 384, 385.5, 407.1, 365; 156/250, 256, 269

(56) References Cited

U.S. PATENT DOCUMENTS

| | | |
|---|---|---|
| 3,498,860 A | 3/1970 | Pickett |
| 3,810,874 A | 5/1974 | Mitsch et al. |
| 4,321,404 A | 3/1982 | Williams et al. |
| 4,472,480 A | 9/1984 | Olson |
| 4,567,073 A | 1/1986 | Larson et al. |
| 4,830,910 A | 5/1989 | Larson |
| 4,853,262 A | 8/1989 | Horie et al. |
| 4,904,525 A | 2/1990 | Taniguchi et al. |
| 4,907,090 A | 3/1990 | Ananian |
| 5,002,326 A | 3/1991 | Westfield et al. |
| 5,104,929 A | 4/1992 | Bilkadi |
| 5,175,030 A | 12/1992 | Lu et al. |
| 5,183,597 A | 2/1993 | Lu |
| 5,306,758 A | 4/1994 | Pellerite |
| 5,389,438 A | 2/1995 | Miller et al. |
| RE35,318 E | 8/1996 | Warman |
| 5,648,407 A | 7/1997 | Goetz et al. |
| 5,670,598 A | 9/1997 | Leir et al. |
| 5,677,050 A | 10/1997 | Bilkadi et al. |
| 5,851,664 A | 12/1998 | Bennett et al. |
| 5,851,674 A | 12/1998 | Pellerite et al. |
| 6,004,670 A | 12/1999 | Kobe et al. |
| 6,059,628 A | 5/2000 | Yoo et al. |

(List continued on next page.)

FOREIGN PATENT DOCUMENTS

| | | | |
|---|---|---|---|
| DE | 3637 188 A1 | | 5/1988 |
| JP | 00020240 | | 6/1998 |
| JP | 11101943 | | 4/1999 |
| JP | P2001-83886 A | | 7/1999 |
| JP | P2000-56694 A | | 2/2000 |
| WO | WO 99/37720 | * | 7/1999 |
| WO | WO 9937720 | | 7/1999 |
| WO | WO 9953357 | | 10/1999 |
| WO | WO 9957185 | | 11/1999 |
| WO | WO 9964899 | | 12/1999 |
| WO | WO 0024576 | | 5/2000 |

*Primary Examiner*—Brian K. Talbot
(74) *Attorney, Agent, or Firm*—Stephen W. Buckingham

(57) ABSTRACT

An antisoiling hardcoated film comprising a substantially transparent substrate, a hardcoat layer comprising inorganic oxide particles dispersed in a binder matrix, and an antisoiling layer comprising a perfluoropolyether. The antisoiling layer can be very thin, thus reducing the cost of the perfluoropolyether. The film has very good scratch, smudge and glare resistance and very good interlayer adhesion and durability. The film can be in the form of a single flexible substrate or a stack of such substrates. The film or stack can be sized to fit the display screen of an electronic display device such as a personal digital assistant or cell phone.

13 Claims, 4 Drawing Sheets

U.S. PATENT DOCUMENTS

| | | | |
|---|---|---|---|
| 6,099,682 A | 8/2000 | Krampe et al. | |
| 6,132,861 A | 10/2000 | Kang et al. | |
| 6,197,397 B1 | 3/2001 | Sher et al. | |
| 6,204,350 B1 | 3/2001 | Liu et al. | |
| 6,238,798 B1 | 5/2001 | Kang et al. | |
| 6,245,833 B1 | 6/2001 | Kang et al. | |
| 6,250,765 B1 * | 6/2001 | Murakami | 359/609 |
| 6,329,058 B1 * | 12/2001 | Arney et al. | 428/403 |

* cited by examiner

ANTISOILING HARDCOAT

CROSS-REFERENCE TO RELATED APPLICATION

This application is a divisional of application Ser. No. 09/923,749, filed Aug. 7, 2001, entitled "ANTISOILING HARDCOAT" (now U.S. Pat. No. 6,660,388), which is a continuation-in-part of application Ser. No. 09/633,835, filed Aug. 7, 2000 (now U.S. Pat. No. 6,589,650), the disclosure of which is incorporated by reference herein.

FIELD OF THE INVENTION

This invention relates to protective films and coatings.

BACKGROUND OF THE INVENTION

Optical displays, and especially touch panel displays, typically have an exposed viewing surface made from a thermoplastic film or slab. Commonly-employed thermoplastic polymers have very good optical transparency, dimensional stability and impact resistance, but unfortunately have poor abrasion resistance. The optical displays of devices such as personal digital assistants ("PDAs"), cell phones, touch-sensitive screens and removable computer filters are subjected to frequent handling and contact with the user's face or fingers, styli, jewelry and other objects. For example, facial oils can adversely affect contrast, color saturation or brightness of a cell phone display. The screens of projection televisions and laptop computers are handled less frequently but nonetheless are sometimes touched, scratched or smudged. Consequently, the viewing face of the display is susceptible to scratches, abrasion and smudges arising during routine use. This can cause the display to lose resolution and clarity, and sometimes to become unreadable or inoperative. To protect such displays, protective films or coatings can be employed.

Protective films for PDAs, cellular phones and other display devices are available from many commercial sources including A.R.M. (SECURER™ Screen Protector), CompanionLink Software, Inc. (COMPANIONLINK™ PDA Screen Protector), EC Film (PDA Screen Protector), Fellowes Corporation (WrightRIGHT™ PDA Screen Protector), PerfectData Corporation (SILKYBOARD™ PDA Keyboard and Screen Protector), ROTA Technology Inc. (RT-PDS Screen Protector and RT-MPS Mobile Phone Screen protector), Swann Communications (PDA PLUS™ Screen Protectors), Sanwa Supply Inc. (LCD-PDA Screen Protector) and VSPS (V.S. Protective Shield). Typically these products are sold as single precut sheets of plain plastic film, although some include a textured or tinted surface over at least a portion of the film. Some of the above-mentioned protective films are said to help keep a PDA screen smudge-free. Viewing screen protective devices are also shown in, e.g., U.S. Pat. No. 4,907,090 (Ananian); U.S. Pat. No. 6,059,628 (Yoo et al.); U.S. Pat. No. 6,250,765 (Murakami) and Re. 35,318 (Warman). A touch panel device having a roughened outermost surface is shown in Japanese published patent application (Kokai) No. 2000-020240.

Hardcoats have also been used to protect the face of information displays. These hardcoats typically contain inorganic oxide particles, e.g., silica, of nanometer dimensions dispersed in a binder precursor resin matrix, and sometimes are referred to as "ceramers". For example, U.S. Pat. No. 5,104,929 (Bilkadi '929) describes UV curable ceramer coatings containing colloidal silica particles dispersed in a protic group-substituted ester or amide of an acrylic acid. A ceramer described in Bilkadi '929 and known as 3M 906 Abrasion Resistant Coating has been used as a hardcoat on signage.

U.S. Pat. No. 6,132,861 (Kang et al. '861), U.S. Pat. No. 6,238,798 B1 (Kang et al. '798) and U.S. Pat. No. 6,245,833 B1 (Kang et al. '833) and Published PCT Application No. WO 99/57185 (Huang et al.) describe ceramer compositions containing blends of colloidal inorganic oxide particles, a curable binder precursor and certain fluorochemical compounds. These compositions provide stain and abrasion resistant hardcoats in a single layer coating.

A transparent stack of anti-graffiti sheets is shown in PCT Published Application No. WO 00/24576 (Janssen et al.). The entire stack is applied to a glass or plastic window, signage or a display and the topmost sheet is removed once the sheet has become damaged. The sheets in the stack can include an optional release layer. The release layer is said preferably to comprise a material selected from the group consisting of acrylates, methacrylates, urethanes, polyolefins, silicones, fluorochemicals such as fluorocarbons, and mixtures thereof. In Example 7, 3M 906 Abrasion resistant Coating is employed as an abrasion-resistant release layer atop polycarbonate sheets in the stack. Stacks of removable plastic sheets for use on automotive windows are shown in U.S. Pat. No. 5,002,326 (Westfield et al.) and in Offenlegungsschrift DE 36 37 188 A1 (Altmann et al.).

U.S. Pat. No. 5,851,674 (Pellerite et al.) describes a self-assembling fluorinated silane film that can be applied atop a multilayer antireflective film to provide a coating having antisoiling properties.

U.S. Pat. No. 6,204,350 (Liu et al.) describes curable coating compositions which comprises alkoxysilane containing fluorinated polymers.

SUMMARY OF THE INVENTION

Coatings made from 3M 906 Abrasion Resistant coating are susceptible to smudges, staining and marks from pens or pencils. It can be difficult to mix the ingredients in the Kang et al. '798 and Kang et al. '833 compositions without experiencing flocculation. Owing to the high cost of the fluorochemical and its use throughout the hardcoat layer, these compositions are also relatively expensive. The Pellerite et al. films have insufficient adhesion to a film made from a ceramer such as 3M 906 Abrasion Resistant Coating.

The present invention provides in one aspect a display element comprising a substantially transparent substrate, a hardcoat layer comprising inorganic oxide particles dispersed in a binder matrix, and an antisoiling layer comprising a perfluoropolyether atop the hardcoat.

The invention also provides an information display protector for display devices having an information display area, comprising a flexible substantially transparent generally planar substrate having on one side thereof an adhesive layer and having on the other side thereof a hardcoat layer comprising inorganic oxide particles dispersed in a binder matrix and an antisoiling layer comprising a perfluoropolyether atop the hardcoat.

The invention also provides information display protectors for a portable electronic device having a display screen, comprising a stack of flexible substantially transparent sheets, the sheets having on one side thereof an adhesive layer and having on the other side thereof a hardcoat layer comprising inorganic oxide particles dispersed in a binder matrix and an antisoiling layer comprising a perfluoropolyether atop the hardcoat, the stack being cut so that the sheets will fit the display screen. The stack can conveniently be stored by adhering it to a portion of the display or to a display cover.

The invention also provides an antisoiling hardcoated film, comprising a flexible generally planar substrate having on at least one side thereof a hardcoat layer comprising inorganic oxide particles dispersed in a binder matrix and an antisoiling layer comprising a perfluoropolyether atop the hardcoat.

The present invention also provides a method for making an antisoiling hardcoat comprising coating and curing on a substrate a ceramer coating comprising inorganic oxide particles dispersed in a free-radically polymerizable binder matrix, and coating and curing atop the ceramer coating an antisoiling layer comprising a free-radically polymerizable fluorochemical.

The present invention also provides a method for making a display element comprising applying to a substantially transparent substrate a curable hardcoat layer comprising inorganic oxide particles dispersed in a free-radically polymerizable binder matrix, curing the hardcoat layer, applying to the hardcoat layer a curable antisoiling layer comprising a perfluoropolyether, and curing the antisoiling layer.

In addition, the invention provides a method for making an information display protector for a device having an information display area, comprising:

a) applying to one side of a substantially transparent generally planar substrate a curable hardcoat layer comprising inorganic oxide particles dispersed in a free-radically polymerizable binder matrix, curing the hardcoat layer, applying to the hardcoat layer a curable antisoiling layer comprising a perfluoropolyether, and curing the antisoiling layer; and b) applying to the other side of the substrate an adhesive layer.

The invention also provides a method for making information display protectors for portable electronic devices having an information display area, comprising carrying out steps a) and b) above; forming the coated substrate into a stack of sheets; and converting the stack so that the sheets will fit the information display area.

The invention also provides a continuous, roll to roll manufacturing method for making a roughened screen protector sheet for information displays, comprising:

a) depositing a substantially solvent-free, curable ceramer composition comprising inorganic oxide particles dispersed in a free-radically polymerizable binder matrix into the nip region between a substantially transparent substrate and a roll having an average surface roughness of at least 0.1 micrometer;

b) moving the roll at a sufficient speed and while applying sufficient pressure to the nip to form a bead of the ceramer composition in the nip;

c) curing the ceramer composition through the substrate (using, e.g., ultraviolet radiation) while the ceramer composition is against the roll;

d) removing the cured ceramer coating from the roll;

e) applying to the cured ceramer coating a curable antisoiling layer comprising a perfluoropolyether; and f) curing the antisoiling layer.

The antisoiling layer can be very thin, thus reducing the perfluoropolyether content and cost. The articles of the invention have very good scratch and smudge resistance and very good durability.

DETAILED DESCRIPTION

The display elements of the invention and components thereof are sometimes shown or described herein using words of orientation such as "upper", "atop", "above" or "front". These and similar terms are merely employed for convenience to refer to the general direction (with respect to the optical path through an information display device) towards a normal viewer of the display device. Likewise, the display elements of the invention and components thereof are sometimes shown or described herein using words of orientation such as "lower", "beneath", "underneath" or "behind". These and similar terms are merely employed for convenience to refer to the general direction (with respect to such optical path) towards the display. As will be understood by those skilled in the art, the display elements of the invention can be used in a variety of orientations and locations.

The information display protectors of the invention can be used on a variety of kinds of information displays having a variety of information display area configurations. Such displays include multi-character and especially multi-character, multi-line displays such as liquid crystal displays ("LCDs"), plasma displays, front and rear projection displays, cathode ray tubes ("CRTs") and signage. The information display protectors of the invention can also be used on single-character or binary displays such as light emitting diodes ("LEDs"), signal lamps and switches. The information display protectors of the invention can be used on illuminated or non-illuminated displays. The information display protectors of the invention are especially useful on displays whose information display area is in the form of a viewing screen having a viewing surface that is susceptible to damage during normal use.

The display elements of the invention can be employed in a variety of portable and non-portable information display devices including PDAs, cell phones (including combination PDA/cell phones), touch-sensitive screens, wrist watches, car navigation systems, global positioning systems, depth finders, calculators, electronic books, CD or DVD players, projection television screens, computer monitors, notebook computer displays, instrument gauges, instrument panel covers, signage such as graphic displays (including indoor and outdoor graphics, bumper stickers, and the like), reflective sheeting, and the like. These devices can have planar viewing faces, or non-planar viewing faces such as the slightly curved face of a typical CRT. Typically the display element is located on or in close physical proximity to a viewing face of the information display device rather than being spaced an appreciable distance therefrom.

Figure 1:
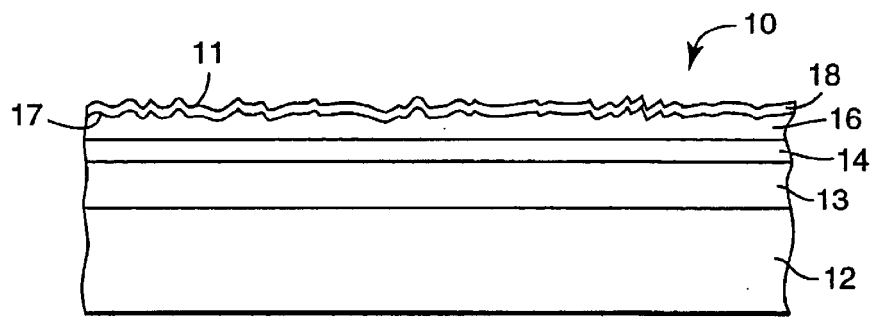
FIG. 1 is a schematic side view of a capacitive touch screen containing a display element of the invention.

Referring now to FIG. 1, a capacitive touch panel display generally identified as 10 is shown in schematic form. Viewing surface 11 permits an observer (not shown in FIG. 1) to see images from imaging device 12. Imaging device 12 can be any of a number of device types capable of displaying information, including transmissive, reflective or transflective liquid crystal displays, cathode ray tubes, micromirror arrays, and printed panels or other backgrounds. Generally planar substrate 13 protects imaging device 12 and provides a support for viewing surface 11. Substrate 13 typically is made of glass or a plastic such as polycarbonate or polyethylene terephthalate. The upper surface of substrate 13 is covered with a transparent thin conductive coating 14. Coating 14 typically is made of a metal or alloy such as indium tin oxide or of a conductive polymer. Hardcoat 16 lies atop coating 14, and provides scratch and abrasion resistance to help protect coating 14 and the underlying substrate 13 from damage. Hardcoat 16 has a roughened upper surface 17. The inclusion of such a roughened surface is optional. It provides glare protection for display 10 and makes it easier to write upon display 10 using a stylus. Antisoiling layer 18 is sufficiently thin so that the roughened upper surface 17 of hardcoat 16 is replicated on viewing surface 11. Antisoiling layer 18 provides oil and ink resistance to help prevent hardcoat 16 from being smudged or otherwise soiled by exposure to contaminants such as skin oils, cosmetics, pencil lead, inks and adventitious dirt. Antisoiling layer 18 can also make the hard coat easier to clean if it is soiled. Thus if necessary, a user can accidentally or deliberately write on the display with a pen or pencil, and easily remove the resulting pencil or ink marks. As will be appreciated by those skilled in the art, electrodes (not shown in FIG. 1) that typically are positioned at the corners of display 10 apply a voltage and charge the conductive coating 14, which acts as a capacitor. The charge is drained and renewed while a controller (also not shown in FIG. 1) measures the amount of current flowing from each electrode. The charging and draining cycle is repeated at a cycle time determined by the controller. Contact by a conductive stylus or finger with the viewing surface 11 increases the capacitance of the conductive coating 14 so that more current flows when a touch occurs. The touch location is determined by comparing current flows from each electrode.

Although not shown in FIG. 1, an optional antistatic coating can be applied atop the hardcoat or atop the antisoiling layer in order to discourage dust and other contaminants from adhering to the display. Also, an additional layer of hardcoat 16 can optionally be formed on the lower surface of substrate 13. This can help protect substrate 13 from damage and can help to reduce glare and ghosting in display 10.

Figure 2:
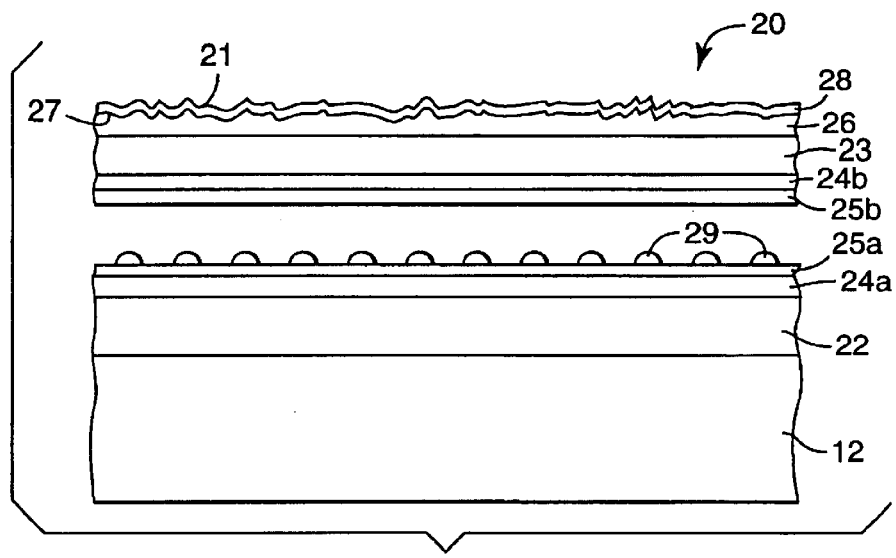
FIG. 2 is a schematic side view of a resistive touch screen containing a display element of the invention.

FIG. 2 shows a resistive touch panel display generally identified as 20 in schematic form. Viewing surface 21 permits an observer (not shown in FIG. 2) to see images from imaging device 12. Substrate 22 of display 10 lies atop imaging device 12 and typically is made of glass or a plastic such as polycarbonate or polyethylene terephthalate. The upper surface of substrate 22 is covered with thin layer of an optional hardcoat 24a, which serves as a primer and adhesion aid for transparent, thin, conductive coating 25a. A similar thin conductive coating 25b is adhered to flexible membrane 23 through optional hardcoat 24b. The upper surface of flexible membrane 23 is coated with hardcoat 26. Hardcoat 26 provides scratch and abrasion resistance to help protect flexible membrane 23 from damage. Hardcoat 26 has an optional roughened upper surface, as in the display of FIG. 1. Antisoiling layer 28 is sufficiently thin so that the roughened upper surface 27 of hardcoat 26 is replicated on viewing surface 21. Antisoiling layer 28 provides oil and ink resistance to help prevent hardcoat 26 from being smudged or otherwise soiled. If desired, an optional antistatic layer can also be provided, as in the display of FIG. 1. Spacers 29 lie atop coating 25a, and a finite space normally separates the upper surface of coating 25a and the lower surface of coating 25b. As will be appreciated by those skilled in the art, contact by a finger or stylus with viewing surface 21 will cause membrane 23 to flex and bring coating 25b into contact with coating 25a, enabling a current to flow between these layers. A controller (not shown in FIG. 2) can identify the touch location by comparing current flowing from various electrodes or busbars (also not shown in FIG. 2) printed on the conductive layers 25a and 25b.

Those skilled in the art will appreciate that other types of touch-sensitive devices can be used in the invention. For example, the touch-sensitive device can operate via guided acoustic wave, surface acoustic wave or near field imaging. The touch-sensitive device can also operate via a non-contact mechanism such as a scanning infrared sensor, e.g., via provision of a suitable array of light beams and photosensors above the upper face of the display.

Figure 3:
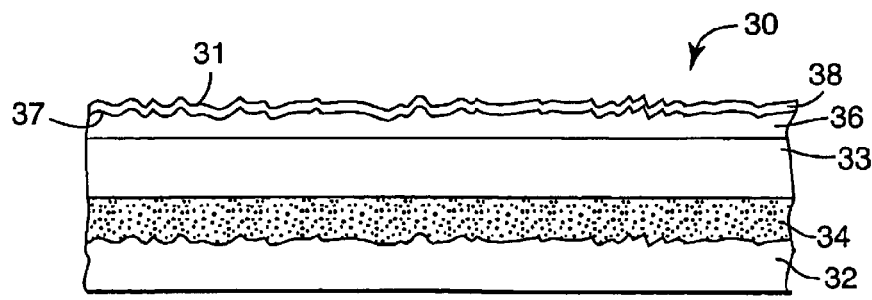
FIG. 3 is a schematic side view of an information display protector of the invention.

FIG. 3 shows an information display protector of the invention generally identified as 30. The lower face of flexible membrane 33 is coated with an adhesive layer 34 to which has been applied a protective liner 32. The lower surface of adhesive 34 is microtextured. Use of a microtextured adhesive layer is optional. Microtexturing helps air bubbles escape from beneath protector 30 when it is applied to a display screen, thereby helping to provide good optical coupling between protector 30 and the screen. The upper face of membrane 33 is coated with a hardcoat layer 36. Hardcoat 36 provides scratch and abrasion resistance to help protect a display screen from damage. Hardcoat 36 has an optional roughened upper surface 37, thus providing glare protection for a display screen. Antisoiling layer 38 is sufficiently thin so that the roughened upper surface 37 of hardcoat 36 is replicated on viewing surface 31 of protector 30. An antistatic layer can also be provided if desired.

Figure 4:
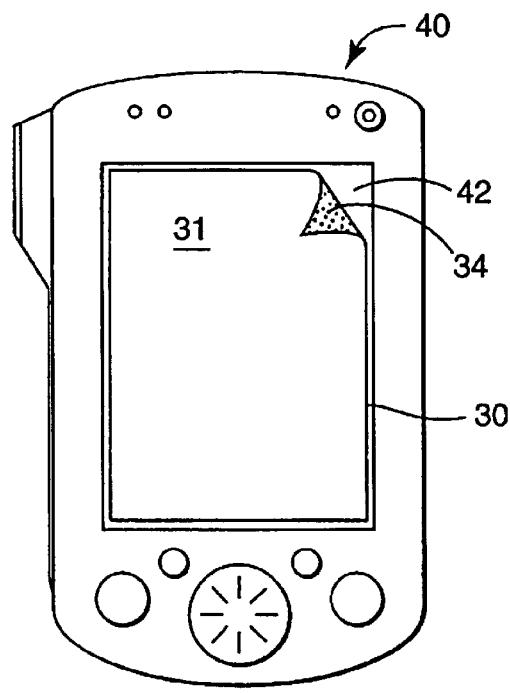
FIG. 4 is a plan view of a PDA, the screen being covered with an information display protector of FIG. 3.

FIG. 4 shows a PDA generally designated as 40 to which has been applied the information display protector 30 of FIG. 3. The user simply removes liner 32 from adhesive 34, centers protector 30 over screen 42 and presses protector 30 into place. Protector 30 serves as a screen protector for the PDA screen, and preferably is precut to slightly undersized dimensions so that the edges of protector 30 extend nearly to the perimeter of screen 42, while still permitting protector 30 to be easily removed later if desired. The roughened viewing surface 31 reduces glare and makes it much easier to write upon screen 42, especially when using a stylus. The antisoiling layer 38 (not shown in FIG. 4) provides oil and ink resistance to help prevent hardcoat 36 (also not shown in FIG. 4) of protector 30 from becoming smudged or otherwise soiled. This is especially helpful if a user accidentally uses a pen or pencil rather than a stylus to write on screen 42.

Figure 5:
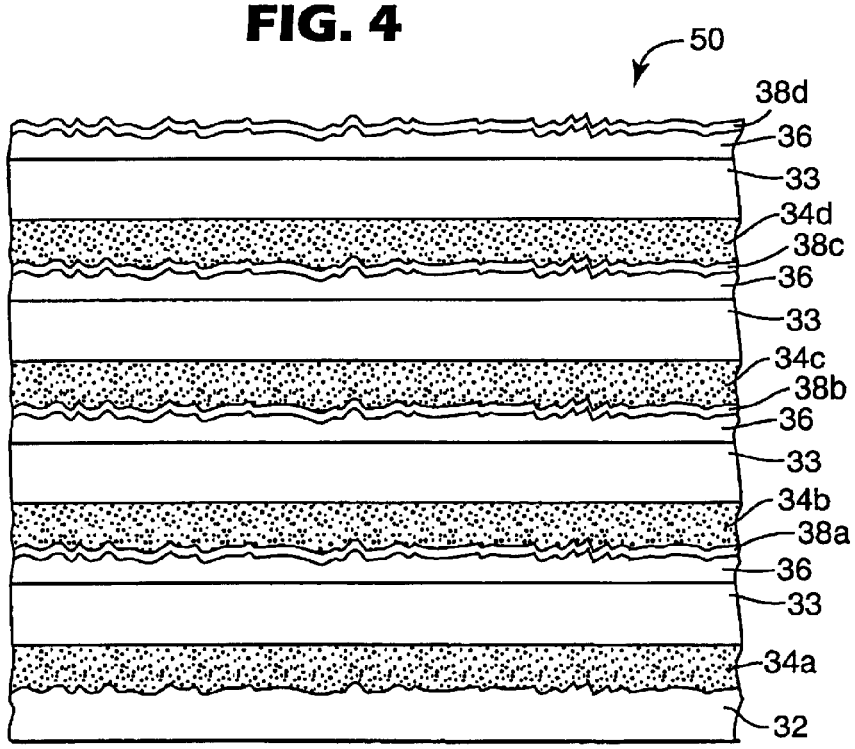
FIG. 5 is a schematic side view of a stack of screen protectors of the invention.

FIG. 5 shows a stack 50 of four PDA information display protectors of the type shown in FIG. 3. Stack 50 has a single liner 32 protecting the adhesive layer 34a of the lowermost information display protector. The remaining information display protectors can be adhered to one another by pressing adhesive layers 34b, 34c and 34d against antisoiling layers 38a, 38b and 38c, respectively. A user can remove the uppermost protector from the stack and adhere it to the screen of a PDA as in FIG. 4. If the thus—applied protector later becomes worn or damaged, it can be peeled off the PDA screen and replaced with another protector from stack 50.

Figure 6:
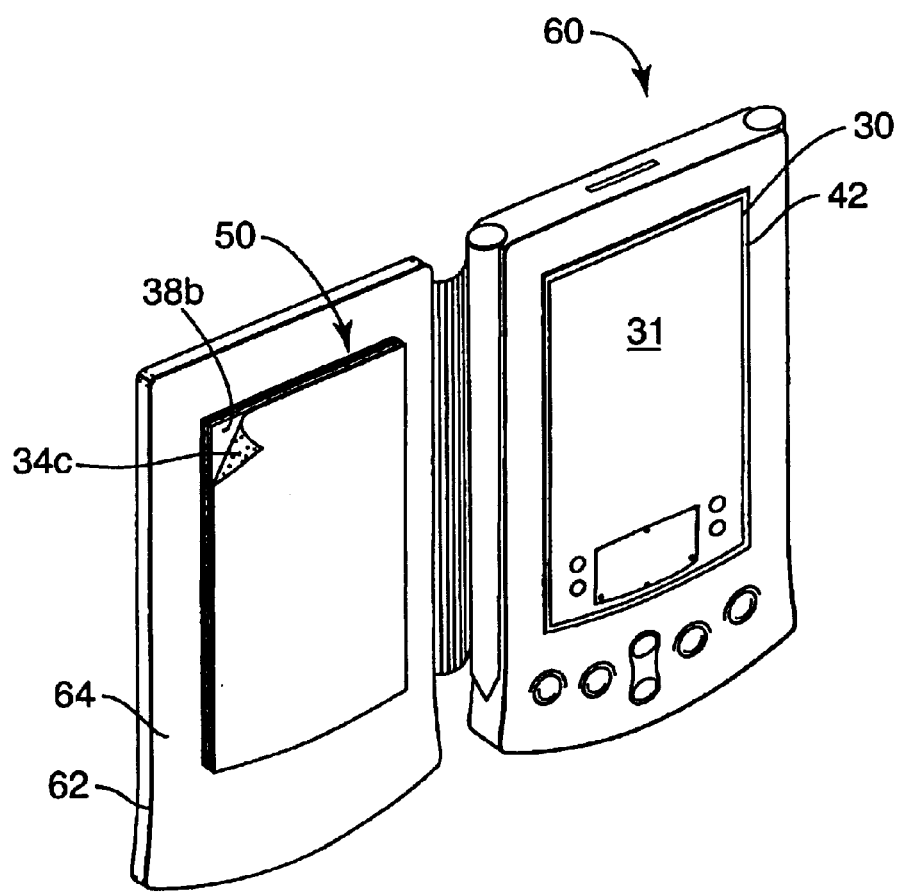
FIG. 6 is a perspective view of a PDA, the screen being covered with an information display protector of FIG. 3, and the inside front cover having a stack of the protectors of FIG. 5 adhered thereto.

A user can store the stack by adhering it to a display device or to its case or cover. FIG. 6 shows a PDA generally designated as 60. Protector 30 (on substrate 33) has been removed from the top of stack 50 and applied to the screen 42 of PDA 60. Liner 32 has been removed from stack 50 so that stack 50 could be adhered to inside surface 64 of PDA front cover 62. Although not shown in FIG. 6, the stack could instead be adhered to the rear of PDA 60 or to any available surface of a separate PDA case. If the stack 50 contains a relatively low number of protectors (e.g., 10 or less, more preferably 5 or less), it will not unduly obscure underlying printed graphics on the front cover (such as the printed GRAFFITI™ alphabet symbol guide that is supplied with some PDAs) and will not hamper closure of a PDA cover or case if applied to an inside surface thereof. Because the stack 50 can be stored with the PDA, spare protectors 30 are close at hand when needed. This is a much more convenient mode of storage than the typical storage mode for current PDA screen protector products sold as single sheets. When protector 30 on screen 42 becomes worn or damaged, a fresh protector can be removed from stack 50. For example, as shown in FIG. 6, the next protector in stack 50 can be removed by peeling adhesive layer 34c away from antisoiling layer 38b.

Figure 7:
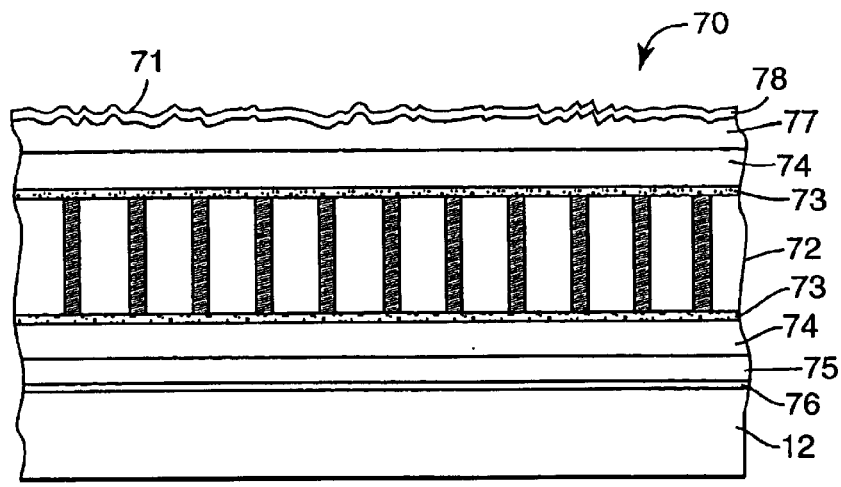
FIG. 7 is a schematic side view of a removable computer privacy filter containing a display element of the invention.

FIG. 7 shows a removable computer privacy filter generally identified as 70. Louvered light control film 72 permits a viewer to see images from an underlying imaging device 12 through viewing surface 71, while preventing an observer located away from the main viewing axis from seeing such images. Substrate layers 74 are adhered to the upper and lower surfaces of light control film 72 by adhesive layers 73. Hardcoats 75 and 77 help to protect the substrate layers 74 and film 72 from damage, and antisoiling layers 76 and 78 provide oil and ink resistance to help prevent hardcoats 75 and 77 from becoming smudged or otherwise soiled. Hardcoat 77 and its antisoiling layer 78 preferably are roughened in order to provide glare reduction. Because filter 70 may frequently be removed from and replaced on a display, the use of the hardcoat and antisoiling layer on both major surfaces of the filter facilitates handling and cleaning even if the user accidentally grips the front and back of the filter rather than handling it by its edges. An optional antistatic coating (not shown in FIG. 7) can also be employed on or just below one or both major surfaces of the filter if desired.

Figure 8:
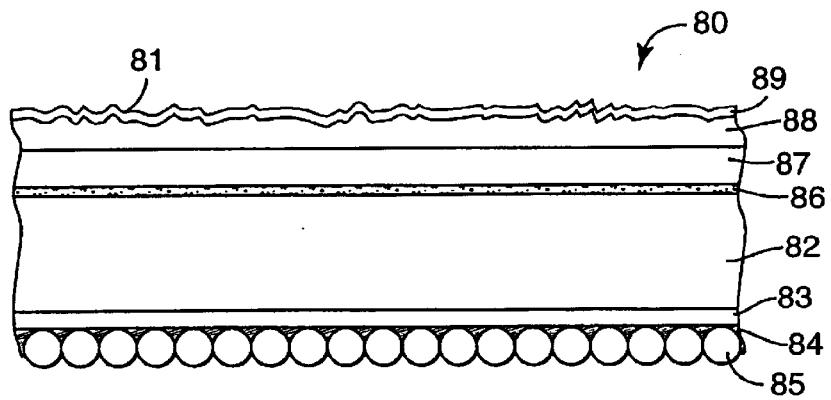
FIG. 8 is a schematic side view of an extended resolution video screen containing a display element of the invention.

FIG. 8 shows an extended resolution video screen generally identified as 80. The rear surface of acrylic screen 82 is covered with a thermoplastic layer of polyvinyl butyral 83 that has been hot-laminated to a monolayer of small glass beads 85 bonded in a contrast-enhancing carbon black-containing urethane bead bond layer 84. Substrate 87 is adhered to the upper surface of screen 82 by adhesive layer 86. Substrate 87 can also be hot-laminated to the upper surface of screen 82. Hardcoat 88 helps to protect substrate 87 and screen 82 from damage, and antisoiling layer 89 provides oil and ink resistance to help prevent hardcoat 88 from becoming smudged or otherwise soiled. Hardcoat 88 and antisoiling layer 89 preferably are roughened in order to provide glare reduction at the viewing surface 81 of screen 80. An optional antistatic coating (not shown in FIG. 8) can also be employed on or just below viewing surface 81 if desired.

A wide variety of substrate materials can be used in the invention. The substrate should be substantially transparent, that is, the substrate should have sufficient transparency or translucency at the intended wavelength and under the intended viewing conditions so that the display element does not unduly impede use and viewing of the underlying information display. Suitable substrate materials include glass, transparent or translucent ceramics, and thermosetting or thermoplastic polymers such as polycarbonate, poly (meth)acrylate (e.g., polymethyl methacrylate or "PMMA"), polyolefins (e.g., polypropylene or "PP"), polyurethane, polyesters (e.g., polyethylene terephthalate or "PET"), polyamides, polyimides, phenolic resins, cellulose diacetate, cellulose triacetate, polystyrenes, styrene-acrylonitrile copolymers, epoxies, and the like. Typically the substrate will be chosen based in part on the desired optical and mechanical properties for the intended use. Such mechanical properties typically will include rigidity, dimensional stability and impact resistance. The substrate thickness typically also will depend on the intended use. For most applications, substrate thicknesses of less than about 1 mm are preferred, more preferably less than about 0.1 mm and most preferably about 0.02 to about 0.2 mm. The substrate can be flexible or rigid. Flexible substrates in the form of self-supporting polymeric films are preferred. Flexible films made from polyesters such as PET or polyolefins such as PP (polypropylene), PE (polyethylene) and PVC (polyvinyl chloride) are particularly preferred. The substrate can be formed into a film using conventional filmmaking techniques such as extrusion of the substrate resin into a film and optional uniaxial or biaxial orientation of the extruded film. The substrate can be treated to improve adhesion between the substrate and the hardcoat, using, e.g., chemical treatment, corona treatment such as air or nitrogen corona, plasma, flame, or actinic radiation. If desired, an optional tie layer can also be applied between the substrate and the hardcoat to increase the interlayer adhesion. The other side of the substrate may also be treated using the above-described treatments to improve adhesion between the substrate and the adhesive.

The hardcoat is a tough, abrasion resistant layer that protects the substrate and the underlying information display from damage from causes such as scratches, abrasion and solvents. The hardcoat preferably contains nanometer-sized inorganic oxide particles dispersed in a binder matrix. Typically the hardcoat is formed by coating a curable liquid ceramer composition onto the substrate and curing the composition in situ to form a hardened film. Suitable coating methods include, for example, spin coating, knife coating, die coating, wire coating, flood coating, padding, spraying, roll coating, dipping, brushing, foam application, and the like.

A variety of inorganic oxide particles can be used in the hardcoat. The particles preferably are substantially spherical in shape and relatively uniform in size. The particles can have a substantially monodisperse size distribution or a polymodal distribution obtained by blending two or more substantially monodisperse distributions. Preferably the inorganic oxide particles are and remain substantially non-aggregated (substantially discrete), as aggregation can result in precipitation of the inorganic oxide particles or gelation of the hardcoat. Preferably the inorganic oxide particles are colloidal in size, that is, they preferably have an average particle diameter of about 0.001 to about 0.2 micrometers, more preferably less than about 0.05 micrometers, and most preferably less than about 0.03 micrometers. These size ranges facilitate dispersion of the inorganic oxide particles into the binder resin and provide ceramers with desirable surface properties and optical clarity. The average particle size of the inorganic oxide particles can be measured using transmission electron microscopy to count the number of inorganic oxide particles of a given diameter. Preferred inorganic oxide particles include colloidal silica, colloidal titania, colloidal alumina, colloidal zirconia, colloidal vanadia, colloidal chromia, colloidal iron oxide, colloidal antimony oxide, colloidal tin oxide, and mixtures thereof. The inorganic oxide particles can consist essentially of or consist of a single oxide such as silica, or can comprise a combination of oxides, such as silica and aluminum oxide, or a core of an oxide of one type (or a core of a material other than a metal oxide) on which is deposited an oxide of another type. Silica is a particularly preferred inorganic particle. The inorganic oxide particles are desirably provided in the form of a sol containing a colloidal dispersion of inorganic oxide particles in liquid media. The sol can be prepared using a variety of techniques and in a variety of forms including hydrosols (where water serves as the liquid medium), organosols (where organic liquids so serve), and mixed sols (where the liquid medium contains both water and an organic liquid), e.g., as described in U.S. Pat. No. 5,648,407 (Goetz et al.) and U.S. Pat. No. 5,677,050 (Bilkadi et al.), the disclosure of which is incorporated by reference herein. Aqueous sols of amorphous silica are particularly preferred. Preferred sols generally contain from about 2 to about 50 weight percent, preferably from about 25 to about 45 weight percent, of colloidal inorganic oxide particles based on the total weight of the sol. Preferred sols can be obtained from suppliers such as ONDEO Nalco Co. (for example, NALCO™ 1040, 1042, 1050, 1060, 2327, and 2329 colloidal silicas), Nyacol Nano Technologies, Inc. (for example, NYACOL™ AL20 colloidal alumina and NYACOL™ A1530, A1540N, and A1550 colloidal antimony pentoxides), and W.R. Grace and Co. (for example, LUDOX™ colloidal silicas). The surface of the inorganic particles can be "acrylate functionalized" as described in Bilkadi et al. The sols can also be matched to the pH of the binder, and can contain counterions or water-soluble compounds (e.g., sodium aluminate), all as described in Kang et al. '798.

The hardcoat can conveniently be prepared by mixing an aqueous sol of inorganic oxide particles with a free-radically curable binder precursor (e.g., one or more free-radically curable monomers, oligomers or polymers that can participate in a crosslinking reaction upon exposure to a suitable source of curing energy). The resulting composition usually is dried before it is applied, in order to remove substantially all of the water. This drying step is sometimes referred to as "stripping". An organic solvent can be added to the resulting ceramer composition before it is applied, in order to impart improved viscosity characteristics and assist in coating the ceramer composition onto the substrate. After coating, the ceramer composition can be dried to remove any added solvent, and then can be at least partially hardened by exposing the dried composition to a suitable source of energy in order to bring about at least partial cure of the free-radically curable binder precursor.

The hardcoat preferably contains about 10 to about 50, and more preferably about 25 to about 40 parts by weight of inorganic oxide particles per 100 parts by weight of the binder. More preferably the hardcoat is derived from a ceramer composition containing about 15 to about 40% acrylate functionalized colloidal silica, and most preferably about 15 to about 35% acrylate functionalized colloidal silica.

A variety of binders can be employed in the hardcoat. Preferably the binder is derived from a free-radically polymerizable precursor that can be photocured once the hardcoat composition has been coated upon the substrate. Binder precursors such as the protic group-substituted esters or amides of an acrylic acid described in Bilkadi, or the ethylenically-unsaturated monomers described in Bilkadi et al., are especially preferred. Suitable binder precursors include polyacrylic acid or polymethacrylic acid esters of polyhydric alcohols, such as diacrylic acid or dimethylacrylic acid esters of diols including ethyleneglycol, triethyleneglycol, 2,2-dimethyl-1,3-propanediol, 1,3-cyclopentanediol, 1-ethoxy-2,3-propanediol, 2-methyl-2,4-pentanediol, 1,4-cyclohexanediol, 1,6-hexamethylenediol, 1,2-cyclohexanediol, 1,6-cyclohexanedimethanol, resorcinol, pyrocatechol, bisphenol A, and bis(2-hydroxyethyl) phthalate; triacrylic acid or trimethacrylic acid esters of triols including glycerin, 1,2,3-propanetrimethanol, 1,2,4-butanetriol, 1,2,5-pentanetriol, 1,3,6,-hexanetriol, 1,5,10-decanetriol, pyrogallol, phloroglucinol, and 2-phenyl-2,2-methylolethanol; tetraacrylic acid or tetramethacrylic acid esters of tetraols including 1,2,3,4-butanetetrol, 1,1,2,2,-tetramethylolethane, 1,1,3,3,-tetramethylolpropane, and pentaerythritol tetraacrylate; pentaacrylic acid or pentamethacrylic acid esters of pentols including adonitol; hexaacrylic acid or hexamethacrylic acid esters of hexanols including sorbitol, dipentaerythritol, dihydroxy ethyl hydantoin; and mixtures thereof. The binder can also be derived from one or more monofunctional monomers as described in Kang et al. '798. Preferably the binder comprises one or more N,N-disubstituted acrylamide and or N-substituted-N-vinyl-amide monomers as described in Bilkadi et al. More preferably the hardcoat is derived from a ceramer composition containing about 20 to about 80% ethylenically unsaturated monomers and about 5 to about 40% N,N-disubstituted acrylamide monomer or N-substituted-N-vinyl-amide monomer, based on the total weight of the solids in the ceramer composition.

Preferably the inorganic particles, binder and any other ingredients in the hardcoat are chosen so that the cured hardcoat has a refractive index close to that of the substrate. This can help reduce the likelihood of Moiré patterns or other visible interference fringes.

As mentioned above, the hardcoat can be formed from an aqueous coating composition that is stripped to remove water prior to coating, and optionally diluted with a solvent to assist in coating the composition. Those skilled in the art will appreciate that selection of a desired solvent and solvent level will depend on the nature of the individual ingredients in the hardcoat (or tie layer) and on the desired substrate and coating conditions. Kang et al. '798 describes several useful solvents, solvent levels and coating viscosities.

The hardcoat can be crosslinked with various agents to increase the internal cohesive strength or durability of the hardcoat. Preferred crosslinking agents have a relatively large number of available functional groups, and include tri and tetra-acrylates, such as pentaerythritol triacrylate and pentaerythritol tetraacrylate. When used, the crosslinking agent preferably is less than about 60 parts, and more preferably about 30 to about 50 parts by weight per 100 parts by weight of the binder.

Those skilled in the art will also appreciate that the hardcoat can contain other optional adjuvants, such as surface treatment agents, surfactants, antistatic agents (e.g., conductive polymers), leveling agents, initiators (e.g., photoinitiators), photosensitizers, UV absorbers, stabilizers, antioxidants, fillers, lubricants, pigments, dyes, plasticizers, suspending agents and the like. Kang et al. '798 contains an extensive discussion of such adjuvants and recommended use levels.

If the hardcoat is prepared by combining an aqueous sol of colloidal inorganic oxide particles with the binder precursor, then preferably the sol has a pH such that the particles have a negative surface charge. For example, if the inorganic particles are predominantly silica particles, the sol preferably is alkaline with a pH greater than 7, more preferably greater than 8, and most preferably greater than 9. Preferably the sol includes ammonium hydroxide or the like so that $NH_4^+$ is available as a counter cation for particles having a negative surface charge. If surface treatment of the colloidal inorganic oxide particles is desired, a suitable surface treatment agent can be blended into the sol, e.g., as described in Kang et al. '833, the disclosure of which is incorporated by reference herein. The free-radically curable binder precursor is then added to the ceramer composition. The ceramer composition is stripped to remove substantially all of the water. For example, removing about 98% of the water, thus leaving about 2% water in the ceramer composition, has been found to be suitable. As soon as substantially all of the water is removed, an organic solvent of the type described in Kang et al. '798 preferably is added in an amount such that the ceramer composition includes from about 5% to about 99% by weight solids (preferably about 10 to about 70%). After adding the solvent, any other desired adjuvants can be added.

Preferably the ceramer composition is coated at a coating weight sufficient to provide a cured hardcoat with a thickness of about 1 to about 100 micrometers, more preferably about 2 to about 50 micrometers, and most preferably about 3 to about 30 micrometers. After coating, the solvent, if any, is flashed off with heat, vacuum, and/or the like. The coated ceramer composition is then cured by irradiation with a suitable form of energy, such as heat energy, visible light, ultraviolet light or electron beam radiation. Irradiating with ultraviolet light in ambient conditions is presently preferred due to the relative low cost and speed of this curing technique. In addition, the hardcoat surface optionally is roughened or textured to provide a matte surface. This can be accomplished in a variety of ways that will be familiar to those skilled in the art, including embossing the hardcoat with a suitable tool that has been bead-blasted or otherwise roughened, by adding a suitable small particle filler such as silica sand or glass beads to the hardcoat, or by carrying out cure against a suitable roughened master as described in U.S. Pat. No. 5,175,030 (Lu et al.) and U.S. Pat. No. 5,183,597 (Lu).

The antisoiling layer comprises a perfluoropolyether. Preferred perfluoropolyethers contain randomly distributed perfluoroalkylene oxide —$(C_nF_{2n}O)$— repeating units such as —$CF_2O$— or —$[(CF_2)_nCF_{2-m}(CF_3)_mO]$— (in which m is 0 or 1 and n is preferably 1 to 7), and pendent (e.g., terminal) polymerizable (e.g., acrylate or methacrylate) groups. Suitable perfluoropolyethers include those described in U.S. Pat. No. 3,810,874 (Mitsch et al.), U.S. Pat. No. 4,321,404 (Williams et al.), U.S. Pat. No. 4,472,480 (Olson), U.S. Pat. No. 4,567,073 (Larson et al. '073), U.S. Pat. No. 4,830,910 (Larson et al. '910) and U.S. Pat. No. 5,306,758 (Pellerite), the disclosures of which are incorporated by reference herein. One preferred subclass of antisoiling layers is derived from perfluoropolyethers of the formula:

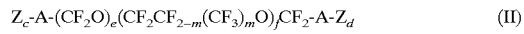   (I)

wherein each Y comprises a polymerizable group attached to a chain of randomly distributed, —$C_aF_{2a}O$—, repeating units, wherein each a is independently 1 to 7, b is the number of such repeating units, and b has a value from 1 to 300 such that the perfluoropolyether has a number average molecular weight of about 500 to about 20,000.

Another preferred subclass of antisoiling layers is derived from perfluoropolyethers of the formula:

$Z_c$-A-$(CF_2O)_e(CF_2CF_{2-m}(CF_3)_mO)_fCF_2$-A-$Z_d$   (II)

wherein each Z is an acrylate or methacrylate group; m is 0 or 1; c and d are 0 to 3 with the proviso that c+d is at least 2; e and f are greater than 5 when M is zero; e can be zero and f is greater than 5 when m is one; and each A is a c+1 or d+1 valent linking group such as. Preferred linking groups A include:

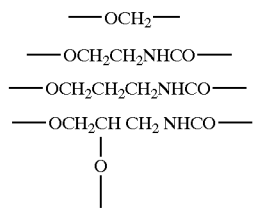

and the like.

Another preferred subclass of preferred antisoiling layers is derived from perfluoropolyethers of the formula:

Y—$(CF_2O)_g(CF_2CF_2O)_nCF_2$—Y   (III)

wherein each Y is as defined above, and g and h are greater than 5. Perfluoropolyethers in this class wherein Y is an acrylate group can be converted from perfluoropolyether diesters of the formula:

$CH_3OOC(CF_2O)_g(CF_2CF_2O)_nCF_2COOCH_3$   (IV)

which are commercially available as FOMBLIN™ diesters from Ausimont USA.

A further preferred subclass of antisoiling layers is derived from perfluoropolyethers of the formula:

Y—$(CF_2CFCF_3O)_gCFCF_3$—Y   (VI)

wherein each Y and g are as defined above. Perfluoropolyethers in this class wherein Y is an acrylate group can be converted from perfluoropolyether diesters of the formula:

$CH_3OOC(CF_2CFCF_3O)_gCFCF_3COOCH_3$   (VI)

which are commercially available as KRYTOX™ diesters from E. I. du Pont de Nemours Co.

Especially preferred perfluoropolyethers include:

$(C_2H_5O)_2CH_3SiC_3H_6NHCO(CF_2O)_{15}(C_2F_4O)_{13}CF_2CONHC_3H_6SiCH_3(OC_2H_5)_2$, $(C_2H_5O)_3SiC_3H_6NHCO(CF_2O)_{15}(C_2F_4O)_{13}CF_2CONHC_3H_6Si(OC_2H_5)_3$, $F(CF(CF_3)CF_2O)_{25}CF2CF_3$, $C_4H_9NHCO(CF_2O)_{15}(C_2F_4O)_{13}CF_2CONHC_4H_9$, $CH_2$=$CHCOOC_2H_4NHCO(CF_2O)_{15}(C_2F_4O)_{13}CF_2CONHC_2H_4OOCCH$=$CH_2$, $CH_2$=$CHCOOCH_2(CF_2O)_{15}(C_2F_4O)_{13}CF_2CH_2OOCCH$=$CH_2$, $(HOCH_2)_2CH_2NHCO(CF_2O)_{15}(C_2F_4O)_{13}CF_2CONHCH_2(CH_2OH)_2$, $(C_2H_5O)_3Si(CH_2)_3NHCO(CF_2CF_2O)_8CF_2CONH(CH_2)_3Si(OC_2H_5)_3$, $(C_2H_5O)_2CH_3Si(CH_2)_3NHCO(CF_2CF_2O)_8CF_2CONH(CH_2)_3SiCH_3(OC_2H_5)_2$, $(C_2H_5O)_2CH_3Si(CH_2)_3NHCO(CF_2CF_2O)_{14}CF_2CONH(CH_2)_3SiCH_3(OC_2H_5)_2$, $(C_2H_5O)_3Si(CH_2)_3NHCO(CF_2C(CF_3)FO)_{12}CF_2CONH(CH_2)_3Si(OC_2H_5)_3$, $(C_2H_5O)_2CH_3Si(CH_2)_3NHCO(CF_2C(CF_3)FO)_{12}CF_2CONH(CH_2)_3SiCH_3(OC_2H_5)_2$, and,

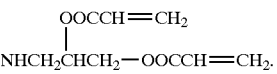

$H_2C=HCCOO-CH_2CHCH_2NHCO(CF_2O)_{15}(CF_2CF_2O)_{13}CF_2CONHCH_2CHCH_2-OOCCH=CH_2$ with OOCCH=CH$_2$ branches.

The antisoiling layer can if desired contain other compatible fluorochemicals such as perfluorinated surfactants, perfluoroalkyl acrylates and perfluoroalkyl methacrylates blended with the perfluoropolyether. Other adjuvants such as soluble or miscible photoinitiators may also be included in the antisoiling layer if desired.

The perfluoropolyether preferably is applied using a solvent that assists in coating the perfluoropolyether onto the hardcoat. Those skilled in the art will appreciate that selection of a desired solvent and solvent level will depend on the nature of the ingredients in the hardcoat and the antisoiling layer and on the desired coating conditions. Preferred solvents include fluorinated solvents such as hydrofluoroethers and perfluorinated octanes (especially when the perfluoropolyether does not contain polar linking groups in its backbone), and hydrocarbon solvents such as methyl ethyl ketone and ethyl acetate, at recommended dissolution levels at or above 20% solids. After adding the solvent, any other desired adjuvants can be added.

The perfluoropolyether can be applied to the hardcoat using a variety of conventional coating methods, including those mentioned above. Gravure, notch-bar, reverse roll coating and curtain coating are preferred. Notch bar and gravure coating are particularly preferred methods as they enable application of a very thin layer, on the order of about 1 to about 5 micrometers wet thickness. Preferably the antisoiling layer is coated at a coating weight sufficient to provide a cured antisoiling layer thickness of about 0.005 to about 2 micrometers, more preferably about 0.01 to about 0.1 micrometers, and most preferably about 0.02 to about 0.08 micrometers. The wet coating is dried, typically using a forced air oven. The dried coating can be further cured (to a partially or completely cured state) using an energy source. Preferred energy sources include ultraviolet light curing devices that provide a UV "C" dosage of about 5 to 60 milliJoules per square centimeter (mJ/cm$^2$). Preferably curing takes place in an environment containing low amounts of oxygen, e.g., less than about 100 parts per million. Nitrogen gas is a preferred environment.

The display element optionally can include an adhesive on the backside of the substrate. Preferably the adhesive is transparent or sufficiently translucent so that it will not unduly hamper viewing of an underlying display device. The adhesive can be derived from a natural product (e.g., a rubber-base adhesive) or can be a synthetic material such as a homopolymer, random copolymer, graft copolymer, or block copolymer. The adhesive can be crosslinked or uncrosslinked, and if desired can have pressure-sensitive properties. An accepted quantitative description for pressure sensitive adhesives (PSAs) is given by the Dahlquist criterion, which indicates that materials having a storage modulus (G') of less than about 3×10$^5$ Pascals (measured at 10 radians/second at room temperature, about 20° to 22° C.) have pressure sensitive adhesive properties while materials having a G' in excess of this value do not. Non-pressure sensitive adhesives are preferred, especially those that provide selective adhesion, e.g., adhesives that have low tack or are non-tacky with respect to skin but have high tack with respect to a targeted surface such as the surface of a display. Display elements coated with such non-pressure sensitive selective adhesives can be easily handled and applied to a display surface, and can be cleanly removed if needed. Suitable low tack or non-tacky adhesives include those described in U.S. Pat. No. 5,389,438 (Miller et al.), U.S. Pat. No. 5,851,664 (Bennett et al.), U.S. Pat. No. 6,004,670 (Kobe et al.) and U.S. Pat. No. 6,099,682 (Krampe et al.). Thermoplastic block copolymer elastomers (copolymers of segmented A and B blocks or segments, displaying both thermoplastic and elastomeric behavior) are especially preferred. Useful thermoplastic block copolymer elastomers include multi-block copolymers having radial, linear A-B diblock, and linear A-B-A triblock structures, as well as blends of such copolymers. Suitable commercially available thermoplastic block copolymer elastomers include the SOLPRENE™ family of materials (Philips Petroleum Co.), the FINAPRENE™ family of materials (FINA), the TUFPRENE™ and ASAPRENE™ family of materials (Asahi), the STEREON™ family of materials (Firestone Synthetic Rubber & Latex Co.), the EUROPRENE SOL T™ family of materials (Enichem), the VECTOR™ family of materials (Dexco Polymers), and the CARIFLEX TR™ family of materials (Shell Chemical Co.). Other suitable adhesive materials include highly crosslinked acrylic adhesives, silicone polyurea elastomers such as are described in U.S. Pat. No. 5,670,598 (Leir et al.), the SEPTON™ family of materials (Kuraray Co. Ltd.) and the KRATON™ family of materials (Shell Chemical Co.) such as KRATON D-1101, D-1102, D-1107, D-1111, D-1112, D-1113, D-1114PX, D-1116, D-1117, D-1118, D-1119, D-1122X, D-1124, D-1125PX, D-1160, D-1165, D-1161, D-1184, D-1193, D-1300, D-1320X, D-4141, D-4158, D-4433, RP-6485, RP-6409, RP-6614, RP-6906, RP-6912, G-1650, G-1651, G-1652, G-1654, G-1657, G-1701, G-1702, G-1726, G-1730, G-1750, G-1765, G-1780, FG-1901, FG-1921, FG-1924, and TKG-101. Mixtures of adhesive materials can also be used.

The adhesive (or a liner that protects the adhesive from contamination and bears against the adhesive) can optionally be microtextured to provide air bleeding and easy handling features (as described, for example, in U.S. Pat. No. 6,197, 397). Typically the adhesive layer of a single sheet or the lowermost layer of a stack of sheets will be covered by a liner. If the adhesive is a tacky adhesive, then the liner preferably has a release coating on the side facing the adhesive, such as a silicone release coating. If the adhesive has low tack or is non-tacky, then a liner made of plain paper or other low surface energy material without a release coating may suffice.

The sheets can be converted (using techniques that will be familiar to those skilled in the art) so that they will fit the information display area of a desired information display device. Suitable conversion techniques include die cutting, slitting and laser cutting.

The present invention will now be further described with reference to the following Examples. Unless otherwise indicated, all parts and percentages are by weight. The following evaluation methods were employed:

Ink Repellency

Figure 9:
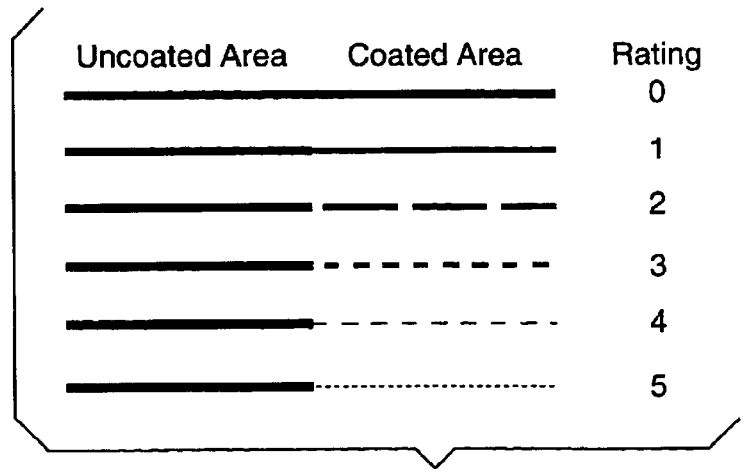
FIG. 9 shows a rating chart used to evaluate ink repellency.

Using a black SHARPIE™ fine point permanent marker (Sanford Corp.), a fine line approximately 3 cm long was drawn from an area not coated with the antisoiling layer onto an area coated with the antisoiling layer. A number value of 0 (completely wettable) to 6 (completely unwettable) was assigned based on the appearance of the resulting line, using the rating chart shown in FIG. 9. Higher numerical values thus represent superior antisoiling performance.

Pencil Hardness

A series of pencils of increasing hardness values ranging from 6B–1B, HB, F, through 1H–9H were fastened in a handheld rolling test stand under a 1 kg applied load and rolled 3 or 5 times across the coated substrates for each tested pencil hardness. The coatings were rated based on the highest pencil hardness that did not scratch or dent the coating. The assigned rating was based on the highest 2 out of three passes when 3 passes were employed and for the highest 3 out of 5 passes when 5 passes were employed. Higher pencil hardness values thus indicate superior film hardness. Desirably a coating should have better than a 3H rating.

Durability

A 2 Kg weight wrapped with dry cheesecloth or a 200 g weight wrapped with Grade 0000 steel wool was rubbed several times back and forth across the coated substrate. Periodically, the rubbing was halted and an attempt was made to write on the rubbed surface using the above-described SHARPIE marker. The assigned durability rating was based on the maximum number of rub cycles for which the ink beaded up and could be wiped off with a dry soft tissue without leaving an ink residue. For some coatings where very high numbers of rub cycles could be performed, rubbing was stopped after many rubs (e.g., 200) and the durability rating was noted as being greater than the number of rubs at which the test was stopped. Desirably a coating should have better than a 40 rub cycle cheesecloth durability rating and better than a 60 rub cycle steel wool durability rating.

Tape Adhesion

Adhesion of the coating layers to the substrate was evaluated by crosshatching the coating with a sharp knife and applying and removing a tape strip to the crosshatched coating, according to ASTM Test Method D3359-97. The amount of coating removed was evaluated using the 5-point scale set out in the Test Method. Peel adhesion was evaluated according to ASTM Test Method D-3330, using an IMASS™ Model SP-2000 peel tester (Imass Inc.) operated at a 2.3 m/min. peel rate (Method A, 180° peel).

Optical Properties

Reflectance was evaluated using an MPC 3100 spectrophotometer (Shimadzu Scientific Instruments. The film sample was adhered to a glass slide whose backside had been coated with black tape. Total reflection and first surface reflection measurements were made and recorded as the percent of incident illumination. Average visible photopic light transmittance, haze and clarity were evaluated using a HAZE-GARD PLUS™ tester (Byk Gardner, Inc.). Gloss was evaluated at 20, 60 or 85 degrees using a MICRO-TRI-GLOSS™ meter (Byk Gardner, Inc.).

EXAMPLES 1–24

A ceramer composition was prepared by first heating 51.5 Parts of the curable binder precursor PETA (pentaerythritol triacrylate) to approximately 49° C. in a reaction vessel. 88 Parts of NALCO™ 2327 colloidal silica sol (a 40% solids, 20 nanometer average particle size silica sol, Nalco Corp.) were added to the PETA. The resulting mixture contained 32.4 parts of colloidal silica particles. 15.6 Parts DMA (N,N-dimethylacrylamide) were next added to the mixture. 0.15 Parts BHT (butylated hydroxytoluene) and 0.02 parts phenothiazine were mixed together and added to the mixture. The mixture was "stripped" by subjecting it to a gentle vacuum distillation (at 100±20 mm Hg and 52°±2° C.) until most of the liquid was removed. A few weight-percent of water remained in the dried product. The resulting dried ceramer precursor was diluted to 50% solids with a 14/1 isopropyl alcohol/distilled water mixture, then further diluted to 25% solids using the same alcohol/water mixture. 0.7 Parts IRGACURE™ 184 photoinitiator (Ciba Specialty Chemicals) were added to the diluted product to provide a photocurable ceramer composition.

The ceramer composition was coated onto 0.04 mm PET film using a Meyer Rod or a gravure roller, at a coating weight sufficient to provide a dried coating thickness of about 3 to about 5 micrometers. The wet coating was dried at 70° C. and cured using a UV H lamp operated at an energy density of 10–60 mJ/cm$^2$ UVC and a nitrogen purge.

An antisoiling layer was applied to the cured hardcoat by dissolving a series of perfluoropolyethers in varying amounts of HFE-7100™ $C_4F_9OCH_3$ hydrofluoroether solvent (3M) and coating the resulting solutions onto the cured hardcoat samples using a Meyer Rod at a coating weight sufficient to provide a dried coating thickness of about 0.03 to about 0.2 micrometers. The wet coating was dried at 70° C. and cured using a UV H lamp operated at an energy density of 5 mJ/cm$^2$ UVC under a nitrogen purge.

Three control compositions and 24 formulations were prepared and evaluated. Set out below in Table 1 for each Control or Example is the coating method used to apply the hardcoat; the identity of the perfluoropolyether, photoinitiator (if any) and adjuvants (if any); and the amount of HFE solvent employed. Set out below in Table 2 are the observed Ink Repellency, Pencil Hardness, and Durability results, and an evaluation of the appearance of the coated Controls and Examples. An entry of "ND" indicates that a value was not determined.

TABLE 1

| Control or Example No. | Ceramer coating method | Parts of Perfluoropolyether (PFPE) | Parts of Photoinitiator in PFPE | Parts of Adjuvant in PFPE | Parts of Solvent |
|---|---|---|---|---|---|
| Control 1 (plain PET) | None | None | | | |
| Control 2 (Ceramer Alone) | Gravure | None | | | |
| Control 3 (No Ceramer) | None | 0.1 PFPE-A[1] | 0.0015 R2074[8] | | 20 HFE[14] |
| 1 | Meyer Rod | 0.1 PFPE-A | 0.0015 R2074 | | 20 HFE |
| 2 | Meyer Rod | 0.1 PFPE-A | 0.0015 R2074 | | 40 HFE |
| 3 | Meyer Rod | 0.1 PFPE-B[2] | 0.0015 R2074 | | 40 HFE |
| 4 | Meyer Rod | 0.1 PFPE-A | 0.0015 R2074 | 0.01 A174[12] | 40 HFE |
| 5 | Meyer Rod | 0.1 PFPE-A/ 0.01 PFPE-C[3] | 0.0015 R2074 | | 40 HFE |
| 6 | Meyer Rod | 0.1 PFPE-A/ 0.01 PFPE-D[4] | 0.0015 R2074 | | 40 HFE |
| 7 | Gravure | 0.1 PFPE-A/ 0.1 PFPE-E[5] | 0.0015 R2074/ 0.004 DEAP[9] | | 40 HFE |
| 8 | Gravure | 0.1 PFPE-F[6] | | | 20 HFE |
| 9 | Gravure | 0.1 PFPE-F | | | 40 HFE |
| 10 | Gravure | 0.1 PFPE-F | 0.004 D-1173[10] | | 40 HFE |
| 11 | Gravure | 0.1 PFPE-E | 0.004 I-184[11] | | 40 HFE |
| 12 | Gravure | 0.1 PFPE-E | 0.004 I-184 | | 20 HFE |
| 13 | Gravure | 0.1 PFPE-E | 0.004 I-184 | | 80 HFE |
| 14 | Gravure | 0.1 PFPE-E | 0.004 D-1173 | | 40 HFE |
| 15 | Gravure | 0.1 PFPE-E | 0.004 D-1173 | | 20 HFE |
| 16 | Gravure | 0.1 PFPE-E | 0.004 D-1173 | | 80 HFE |
| 17 | Gravure | 0.1 PFPE-E | 0.004 D-1173 | | 160 HFE |
| 18 | Gravure | 0.1 PFPE-E | 0.004 D-1173 | | 1600 HFE |
| 19 | Gravure | 0.1 PFPE-E | 0.004 D-1173 | 0.04 A174 | 40 HFE |
| 20 | Gravure | 0.1 PFPE-E | 0.004 D-1173 | 0.05 K1514 | 40 HFE |
| 21 | Gravure | 0.1 PFPE-E/ 0.05 PFPE-D | 0.004 D-1173 | | 40 HFE |
| 22 | Gravure | 0.1 PFPE-E/ 0.05 PFPE-A | 0.004 D-1173 | | 40 HFE |
| 23 | Gravure | 0.1 PFPE-E/ 0.05 PFPE-G[6] | 0.004 D-1173 | | 40 HFE |
| 24 | Gravure | 0.1 PFPE-H[7] | 0.004 D-1173 | | 40 HFE |

Notes:
[1]PFPE-A is $(C_2H_5O)_2CH_3SiC_3H_6NHCO(CF_2O)_{15}(C_2F_4O)_{13}CF_2CONHC_3H_6SiCH_3(OC_2H_5)_2$.
[2]PFPE-B is $(C_2H_5O)_3SiC_3H_6NHCO(CF_2O)_{15}(C_2F_4O)_{13}CF_2CONHC_3H_6Si(OC_2H_5)_3$.
[3]PFPE-C is KRYTOX ™ 1514 perfluoroether fluid $F(CF(CF_3)CF_2O)_{25}CF_2CF_3$ (E. I. DuPont de Nemours & Co.).
[4]PFPE-D is $C_4H_9NHCO(CF_2O)_{15}(C_2F_4O)_{13}CF_2CONHC_4H_9$.
[5]PFPE-E is $CH_2\!=\!CHCOOC_2H_4NHCO(CF_2O)_{15}(C_2F_4O)_{13}CF_2CONHC_2H_4OOCCH\!=\!CH_2$.
[6]PFPE-F is $CH_2\!=\!CHCOOCH_2(CF_2O)_{15}(C_2F_4O)_{13}CF_2CH_2OOCCH\!=\!CH_2$.
[7]PFPE-G is $(HOCH_2)_2CH_2NHCO(CF_2O)_{15}(C_2F_4O)_{13}CF_2CONHCH_2(CH_2OH)_2$.
[8]PFPE-H is:

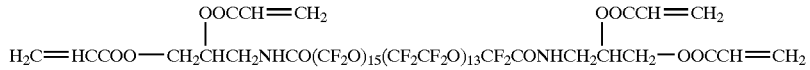

[9]R2074 is RHODORSIL ™ 2074 diaryliodonium tetrakis(pentafluorophenylborate) from Rodia.
[10]DEAP is 2,2-diethoxyacetophenone.
[11]D-1173 is DAROCURE ™ 1173 2-hydroxy-2-methyl-1-phenyl-propan-1-one from Ciba Specialty Chemicals.
[12]I-184 is IRGACURE ™ 184 1-hydroxycyclohexyl phenyl ketone (Ciba Specialty Chemicals).
[13]A-174 is A-174 gamma-methacryloxypropyl trimethoxysilane (Union Carbide Corp.).
[14]HFE is HFE-7100 ™ $C_4F_9OCH_3$ hydrofluoroether solvent (3M).

TABLE 2

| Example No. | Ink Repellency | Hardness | Clarity | Durability, Cheesecloth | Durability, Steel Wool |
|---|---|---|---|---|---|
| Control A | None | HB | Clear | None | None |
| Control B | None | N | Clear | None | None |
| Control C | 4 | ND | Clear | None | None |
| 1 | 5 | ND | Clear | 2 | 7 |
| 2 | 5 | ND | Clear | 5 | 12 |
| 3 | 5 | ND | Clear | 6 | 14 |
| 4 | 4 | ND | Clear | 60 | 100 |
| 5 | 5 | ND | Clear | 15 | 40 |
| 6 | 4 | ND | Clear | 10 | 30 |
| 7 | 4 | ND | S. Haze | 15 | 60 |
| 8 | 5 | >3H | Clear | 250 | 1400 |
| 9 | 5 | >3H | Clear | 200 | 600 |
| 10 | 2 | ND | Haze | ND | ND |
| 11 | 5 | ND | Clear | 300 | 450 |
| 12 | 5 | ND | Clear | 200 | 300 |
| 13 | 5 | ND | Clear | 300 | 450 |
| 14 | 5 | >3H | Clear | 250 | 500 |
| 15 | 5 | ND | Clear | >100 | >500 |
| 16 | 5 | ND | Clear | 250 | 500 |
| 17 | 4 | ND | Clear | 100 | 350 |
| 18 | 1 | ND | Clear | ND | ND |
| 19 | 4 | ND | Clear | 250 | 800 |

TABLE 2-continued

| Example No. | Ink Repellency | Hardness | Clarity | Durability, Cheesecloth | Durability, Steel Wool |
|---|---|---|---|---|---|
| 20 | 4 | ND | S. Haze | >100 | >300 |
| 21 | 5 | ND | Clear | >100 | >600 |
| 22 | 4 | ND | S. Haze | 100 | 200 |
| 23 | 4 | ND | Clear | 300 | >600 |
| 24 | 4 | ND | Clear | 100 | 200 |

Especially good results were obtained using ethylenically unsaturated perfluoroployethers. Although the antisoiling layers were very thin, they formed coatings having very good and very durable ink repellency.

The film of Example 14 was evaluated to determine the average visible photopic light transmittance through the film. The measured transmittance was 93.8%, which is approximately the transmittance (94.5%) of a 0.13 mm thick sample of uncoated PET film.

EXAMPLES 25–32

Using the method of Examples 1–24, display elements were prepared by dissolving varying amounts PFPE-F in HFE-7100 solvent and coating the resulting antisoiling coating solutions onto the cured hardcoat samples at a coating weight sufficient to provide a dried coating thickness of about 0.03 to about 0.2 micrometers. Half of the examples included IRGACURE 184 photoinitiator and half employed no photoinitiator. The wet coatings were dried at 70° C. and cured using a UV H lamp operated at an energy density of 35 mJ/cm$^2$ UVC under a nitrogen purge. Set out below in Table 3 is the amount of perfluoropolyether and photoinitiator for each example, and the observed Durability results.

TABLE 3

| Example No. | PFPE-F, % | Photoinitiator, % | Durability, Cheesecloth | Durability, Steel Wool |
|---|---|---|---|---|
| 25 | 0.25 | None | 200 | 600 |
| 26 | 0.50 | None | 250 | 1400 |
| 27 | 1 | None | 400 | 1000 |
| 28 | 2 | None | 300 | 2000 |
| 29 | 0.25 | 4 | 20 | 60 |
| 30 | 0.50 | 4 | 300 | 1000 |
| 31 | 1 | 4 | 300 | 1800 |
| 32 | 2 | 4 | 400 | 2500 |

The results shown in Table 3 demonstrate very good durability.

EXAMPLES 33–37

Using the method of Examples 1–24, display elements were prepared by dissolving a variety of perfluoropolyethers and 0.01% RHODORSIL 2074 photoinitiator in HFE-7100 solvent and coating the resulting antisoiling coating solutions onto the cured hardcoat samples at a coating weight sufficient to provide a dried coating thickness of about 0.08 micrometers. The wet coatings were dried at 70° C. and cured using a UV H lamp operated at an energy density of 12 mJ/cm$^2$ UVC under a nitrogen purge. Set out below in Table 4 is the identity of the perfluoropolyether and the observed Durability results for each example.

TABLE 4

| Example No. | Perfluoropolyether | Durability, Cheesecloth | Durability, Steel Wool |
|---|---|---|---|
| 33 | PFPE-I[1] | 15 | 50 |
| 34 | PFPE-J[2] | 6 | 8 |
| 35 | PFPE-K[3] | 30 | 15 |
| 36 | PFPE-L[4] | 2 | 12 |
| 37 | PFPE-M[5] | 8 | 19 |

[1]PFPE-I is $(C_2H_5O)_3Si(CH_2)_3NHCO(CF_2CF_2O)_8CF_2CONH(CH_2)_3Si(OC_2H_5)_3$.
[2]PFPE-J is $(C_2H_5O)_2CH_3Si(CH_2)_3NHCO(CF_2CF_2O)_8CF_2CONH(CH_2)_3SiCH_3(OC_2H_5)_2$.
[3]PFPE-K is $(C_2H_5O)_2CH_3Si(CH_2)_3NHCO(CF_2CF_2O)_{14}CF_2CONH(CH_2)_3SiCH_3(OC_2H_5)_2$.
[4]PFPE-L is $(C_2H_5O)_3Si(CH_2)_3NHCO(CF_2C(CF_3)FO)_{12}CF_2CONH(CH_2)_3Si(OC_2H_5)_3$.
[5]PFPE-M is $(C_2H_5O)_2CH_3Si(CH_2)_3NHCO(CF_2C(CF_3)FO)_{12}CF_2CONH(CH_2)_3SiCH_3(OC_2H_5)_2$.

The results shown in Table 4 demonstrate the use of a variety of perfluoropolyethers, applied at a very low coating thickness.

EXAMPLE 38

Using a first vessel placed in an ice bath, one part BAYTRON™ P poly(3,4-ethylene dioxythiophene) poly (styrenesulfonate) conductive polymer solution (Bayer Corp.) was added to the vessel followed by the slow addition of 6.5 parts N,N-dimethylacetamide with mixing. In a second vessel, the stripped, dried ceramer precursor of Examples 1–24 was diluted to 65% solids with a 14:1 isopropyl alcohol/distilled water mixture, and 3.1 parts of the resulting diluted composition was combined with 0.05 parts 2,4,6-trimethylbenzoyldiphenylphosphineoxide photoinitiator. The mixture in the second vessel was then slowly added to the chilled mixture in the first vessel with stirring. The resulting ceramer composition contained 17% solids. It was further diluted with a 72/9/19 isopropyl alcohol/ethanol/n-butyl alcohol solvent mixture to three different solids levels as set out below in Table 5:

TABLE 5

| Ceramer Solution No. | Ceramer | Solvent Mixture | % Solids |
|---|---|---|---|
| 1 | 50 parts | 50 parts | 8.5 |
| 2 | 85 parts | 15 parts | 14.45 |
| 3 | 80 parts | 20 parts | 13.6 |

Using the method of Examples 1–24 and a No. 18 Meyer rod, each of the ceramer solutions was coated onto 0.13 mm thick PET film. The coated PET substrate was dried at 93° C. for 3 minutes, then cured by passing the coatings twice under UV D lamps operated at an energy density of 400–600 mJ/cm$^2$ UVA. The dried ceramer coating thickness was 1 to 2 micrometers. Some samples coated with Ceramer Solution Nos. 2 or 3 were given a second coat and again cured, resulting in a dried ceramer coating thickness of 2 to 4 micrometers. The ceramer-coated samples were next coated with a perfluoropolyether antisoiling coating solution prepared from 1 part PFPE-F ($CH_2$=$CHCOOCH_2(CF_2O)_{15}(C_2F_4O)_{13}CF_2CH_2OOCCH$=$CH_2$), 0.04 parts IRGACURE 184 photoinitiator, 93 parts HFE-7100 solvent and 23 parts methyl ethyl ketone solvent. The perfluoropolyether solution was applied at a coating weight sufficient to give a dried antisoiling coat thickness of about 0.05 to 0.1 micrometers. Using the method of Examples 1–24, the antisoiling coats were dried and cured under UV H lamps operated at an energy density of 10–60 mJ/cm² UVC. Set out below in Table 6 are the ceramer solution numbers, the number of coats of ceramer solution, the ceramer coat thickness, and the conductivity, ink repellency and tape adhesion values for the coated substrates:

TABLE 6

| Ceramer Solution No. | No. of Ceramer Coats | Ceramer Thickness, micrometers | Conductivity | Ink Repellency | Tape Adhesion |
|---|---|---|---|---|---|
| 1 | 1 | 1 to 2 | $1 \times 10^{12}$ | 5 | 5 |
| 2 | 1 | 1 to 2 | $1.5 \times 10^{10}$ | 5 | 5 |
| 2 | 2 | 2 to 4 | $7 \times 10^{9}$ | 5 | 4 |
| 3 | 1 | 1 to 2 | $4 \times 10^{10}$ | 5 | 5 |
| 3 | 2 | 2 to 4 | $1.5 \times 10^{10}$ | 5 | 4 |

EXAMPLE 39

A 3-necked reaction vessel was fitted with a vacuum distillation head and condenser, mechanical stirrer, heating mantle, and thermocouple for controlling the heating. The vessel was charged with 6,718 parts NALCO™ 1042 acidic aqueous sol (pH 3.5 sol from ONDEO Nalco Co., containing 34% of 20 nanometer average diameter silica particles), 1,122 parts hydroxyethyl acrylate, 562 parts 3-(trimethoxysilyl)propyl methacrylate, 2 parts butylated hydroxytoluene, and 0.2 parts phenothiazine. The contents were stirred at room temperature for 1 hour, then heated to 55° C. over about 45 min. The pressure in the vessel was slowly reduced using a vacuum pump to remove volatiles without causing undue foaming. As the foaming subsided, full pump vacuum was applied until nearly all volatiles were removed. This required about 6 to 7 hours of distillation. The vacuum was relieved and then 792 parts SR 444 pentaerythritol triacrylate (Sartomer, Inc.) were added to the vessel. Full pump vacuum was re-applied and the remaining volatiles were removed. When distillation was complete, the contents of the vessel were filtered through fine-mesh cheesecloth to provide a 100% solids solvent-free ceramer hardcoat.

Three chrome-plated metal rolls were roughened using bead-blasting to mean surface roughness (Ra) values of 0.36, 0.44 and 0.57 micrometers, respectively. In a series of runs using one of the roughened metal rolls and a film of 0.05 mm thick polyethylene terephthalate (PET) or 0.13 mm thick polymethyl methacrylate (PMMA), roughened coatings were applied to the films using the above-described solvent-free ceramer hardcoat composition. The roughened coatings were formed by depositing the curable ceramer composition into the nip region between the film and the metal roll, applying pressure to the nip, moving the roll at a speed sufficient to form a bead of the ceramer composition in the nip and curing the ceramer composition through the film using UV D lamps (Fusion Systems, Inc.) operated at an energy density of about 400 mJ/cm² UVA. The cured ceramer coating and film were pulled away from the roll. The surface of the cured ceramer coating replicated the roughened roll surface. Using the method of Example 27, a curable antisoiling layer containing 1% PFPE-F perfluoropolyether in HFE-7100 solvent was applied to and cured on the cured ceramer coating using UV H lamps operated at an energy density of 15 mJ/cm² UVC. The backsides of the coated films were coated with a 35% solution of KRATON™ D-1107 elastomer in toluene, using a fluid bearing die equipped with a 5 micrometer filter, to provide a non-tacky, void-free adhesive coating having a thickness of 0.03 mm.

The coated films were evaluated for reflectance, transmission, haze, clarity, gloss, ink repellency and durability. For comparison, a typical commercially available PDA screen protector (WrightRIGHT™ PDA Screen Protector, Fellowes Corporation) was similarly evaluated. The results are set out below in Table 7.

TABLE 7

| Run No. | Substrate/ Roughness | % Total Reflection | % 1st Surface Reflection | % Trans. | Haze | Clarity | 20° Gloss | 60° Gloss | 85° Gloss | Ink Rep. | Durability, Steel Wool | Pencil Hard. |
|---|---|---|---|---|---|---|---|---|---|---|---|---|
| Control[1] | PVC/ND[2] | 7.186 | 3.999 | 80.2 | 28.2 | 53.6 | 7.9 | 38.3 | 47.8 | 0 | 4 | 2B |
| 39-1 | PET/0.36 | 4.853 | 2.187 | 93.9 | 32.8 | 58.2 | 8.9 | 27.4 | 57 | 5 | 1000 | >3H |
| 39-2 | PET/0.44 | 4.068 | 1.358 | 93.7 | 44.8 | 34.3 | 3.7 | 16.9 | 34 | 5 | 500 | >3H |
| 39-3 | PET/0.57 | 3.899 | 1.205 | 93.6 | 49.5 | 29.8 | 4 | 15.7 | 32.7 | 5 | 1000 | >3H |
| 39-4 | PMMA/0.36 | 4.383 | 1.46 | 95.4 | 32.2 | 57.6 | 9.9 | 28.7 | 61.4 | ND | ND | ND |
| 39-5 | PMMA/0.44 | 3.833 | 1.392 | 95.3 | 43.9 | 34.1 | 4.8 | 18.7 | 43.9 | ND | ND | ND |
| 39-6 | PMMA/0.57 | 3.566 | 1.14 | 95.2 | 48.6 | 29.6 | 4.6 | 16.9 | 38.4 | ND | ND | ND |

[1]WrightRIGHT ™ PDA Screen Protector, Fellowes Corporation.
[2]ND = Not determined.

The adhesive-coated side of the coated PET films was pressed against a plain paper liner, and the films were then die-cut to a rectangular shape to form custom screen protectors sized to fit just inside the perimeter of the screen of a PALM™ Vx PDA (Palm Computing Corp.) like the PDA shown in FIG. 6. The screen protectors covered nearly the entire screen, leaving a small uncovered area between the curved bottom edge of the screen and the chord extending between the endpoints of the bottom edge. The screen protectors were also hand-trimmed to fit just inside the perimeter of the screen of an IPAQ™ color PDA (Compaq Corp.) like the PDA shown in FIG. 4. The screen protector was removed from the liner and pressed into place over the screen of the PDA, using the edge of a credit card to assist in removing air bubbles from under the film. The film provided substantial indoor and outdoor glare reduction without unduly reducing visibility through the PDA screen. When the screen protector of the invention was not present, light reflections made it difficult to read the screen at some angles. The matte finish on the screen protector made it easier to write on the screen using the PDA stylus, because the stylus point had a reduced tendency to skid across the screen. A pen or pencil could also be used to write on the PDA screen protector. A small amount of ink or graphite transferred to the screen protector, but was readily removed using a tissue without leaving any observable damage on the screen protector surface. In contrast, if a pen or pencil is used to write directly on the unprotected PDA screen, the screen typically will be permanently damaged.

EXAMPLE 40

Using standard pad-making equipment, five layers of the adhesive-coated sheet of Example 39 were laminated directly atop one another. The lowermost sheet was laminated to a plain paper liner, and the resulting stacks were die-cut to shape to form pads. The pads were sized to fit just inside the perimeter of the screen of a PALM™ Vx PDA (Palm Computing Corp.) as in Example 39. The liner was removed from the pad and the pad was adhered to the inside front cover of the PDA. The uppermost screen protector was removed from a pad and pressed into place over the screen of the PDA, using the edge of a credit card as in Example 39. The screen protector provided the same advantages as in Example 39, and additional screen protectors could be carried with the PDA so that spares would readily be available.

EXAMPLE 41

In a series of runs, the backside of the coated film of Example 27 was coated using a knife coater with two different adhesives and dried at 70° C. for 15 minutes. The resulting adhesive-coated samples were applied to glass for varying dwell periods and then evaluated for 180° peel adhesion. Set out below in Table 8 is the run number, adhesive identity, dry adhesive thickness and the measured peel adhesion values.

TABLE 8

| | | | 180° Peel Strength, g/mm of width | | | |
|---|---|---|---|---|---|---|
| | | Adhesive | | | | |
| Run No. | Adhesive | Thickness, mm | Initial | 12 hours, 25° C. | 72 hours, 70° C. | 170 hours, 70° C. |
| 1 | RD-975[1] | 0.03 | 58 | 80 | 110 | 103 |
| 2 | RD-975 | 0.05 | 74 | 104 | 132 | 127 |
| 2 | RD-975 | 0.08 | 86 | 117 | 126 | 129 |
| 3 | 1107[2] | 0.05 | 6 | 18 | 19 | 14 |
| 3 | 1107 | 0.08 | 28 | 41 | 39 | 31 |

[1]RD-975 acrylic adhesive (3M).
[2]28% solution of KRATON ™ 1107 elastomer (Shell Chemical Co.) in toluene.

Various modifications and alterations of this invention will be apparent to those skilled in the art without departing from the scope and spirit of this invention. This invention should not be restricted to that set forth herein for illustrative purposes only.

What is claimed is:

1. A method for making an antisoiling hardcoat comprising coating and curing on a substrate a ceramer coating comprising inorganic oxide particles dispersed in a free-radically polymerizable binder matrix, and coating and curing atop the ceramer coating an antisoiling layer comprising a free-radically polymerizable fluorochemical.

2. A method for making a display element comprising applying to a substantially transparent substrate a curable hardcoat layer comprising inorganic oxide particles dispersed in a free-radically polymerizable binder matrix, curing the hardcoat layer, applying directly to the hardcoat layer a curable antisoiling layer comprising a perfluoropolyether, and polymerizing the antisoiling layer.

3. A method according to claim 2 wherein the perfluoropolyether has the formula:

$$Y-(C_aF_{2a}O)_b-C_aF_{2a}-Y$$

wherein each Y comprises a polymerizable group attached to a chain of randomly distributed, $-C_aF_{2a}O-$, repeating units, wherein each a is independently 1 to 7, b is the number of such repeating units, and b has a value from 1 to 300 such that the perfluoropolyether has a number average molecular weight of about 500 to about 20,000.

4. A method according to claim 2 wherein the substrate has first and second major surfaces with the hardcoat being applied to the first major surface, and further comprising applying an adhesive to the second major surface.

5. A method for making a screen protector for an information display, comprising:
   a) applying to one side of a substantially transparent generally planar substrate a curable hardcoat layer comprising inorganic oxide particles dispersed in a free-radically polymerizable binder matrix, curing the hardcoat layer, applying directly to the hardcoat layer a curable antisoiling layer comprising a perfluoropolyether, and polymerizing the antisoiling layer; and
   b) applying to the other side of the substrate an adhesive layer.

6. A method according to claim 5 wherein the perfluoropolyether has the formula:

$$Y-(C_aF_{2a}O)_b-C_aF_{2a}-Y$$

wherein each Y comprises a polymerizable group attached to a chain of randomly distributed, $-C_aF_{2a}O-$, repeating units, wherein each a is independently 1 to 7, b is the number of such repeating units, and b has a value from 1 to 300 such that the perfluoropolyether has a number average molecular weight of about 500 to about 20,000.

7. A method for making screen protectors for portable electronic devices having a display screen, comprising:
   a) applying to one side of a substantially transparent generally planar substrate a curable hardcoat layer comprising inorganic oxide particles dispersed in a free-radically polymerizable binder matrix, curing the hardcoat layer, applying to the hardcoat layer a curable antisoiling layer comprising a perfluoropolyether, and curing the antisoiling layer;
   b) applying to the other side of the substrate an adhesive layer;
   c) forming the coated substrate into a stack of sheets; and
   d) cutting the stack so that the sheets will fit the display screen.

8. A method according to claim 7 wherein the perfluoropolyether has the formula:

$$Y-(C_aF_{2a}O)_b-C_aF_{2a}-Y$$

wherein each Y comprises a polymerizable group attached to a chain of randomly distributed, $-C_aF_{2a}O-$, repeating units, wherein each a is independently 1 to 7, b is the number of such repeating units, and b has a value from 1 to 300 such that the perfluoropolyether has a number average molecular weight of about 500 to about 20,000.

9. A continuous, roll to roll manufacturing method for making a roughened screen protector sheet for information displays, comprising:
   a) depositing a substantially solvent-free, curable ceramer composition comprising inorganic oxide particles dispersed in a free-radically polymemizable binder matrix into the nip region between a substantially transparent substrate and a roll having an average surface roughness of at least 0.1 micrometer;
   b) moving the roll at a sufficient speed and while applying sufficient pressure to the nip to form a bead of the ceramer composition in the nip;

c) photocuring the ceramer composition through the substrate while the ceramer composition is against the roll;

d) removing the cured ceramer coating from the roll;

e) applying to the cured ceramer coating a curable antisoiling layer comprising a perfluoropolyether; and f) curing the antisoiling layer.

10. A method according to claim 9, further comprising converting the coated substrate into sheets sized to fit an electronic display device screen.

11. A method according to claim 10, wherein the device comprises a portable device.

12. A method according to claim 10, wherein the device comprises a personal digital assistant.

13. A method according to claim 9, wherein the sheets are formed into a stack.

* * * * *

UNITED STATES PATENT AND TRADEMARK OFFICE
CERTIFICATE OF CORRECTION

PATENT NO. : 6,841,190 B2
DATED : January 11, 2005
INVENTOR(S) : Liu, Junkang J.

It is certified that error appears in the above-identified patent and that said Letters Patent is hereby corrected as shown below:

Title page,
Item [56], References Cited, FOREIGN PATENT DOCUMENTS, delete "WO  WO 9937720    7/1999"

Column 12,
Line 41, delete "(VI)" and insert -- (V) --, therefor.
Line 59, delete "$F(CF(CF_3)CF_2O)_{25}\mathbf{CF2CF_3}$" and insert
-- $F(CF(CF_3)CF_2O)_{25}CF_2CF_3$ --, therefor.

Column 13,
Line 19, after "and" delete ",".

Column 17,
Table 1, (Notes) Note 3, delete "$F(CF(CF_3)CF_2O)_{25}\mathbf{CF2CF_3}$" and insert
-- $F(CF(CF_3)CF_2O)_{25}CF_2CF_3$ --, therefor.
Table 1, (Notes) Note 11, delete "propan" and insert -- propane -- , therefor.

Column 19,
Line 14, delete "perfluoroployethers" and insert -- perfluoropolyethers --, therefor.

Column 23,
Line 65, delete "$Y—C_aF_{2a}O)_b—C_aF_{2a}—Y$" and insert -- $Y—(C_aF_{2a}O)_b—C_aF_{2a}—Y$ --, therefor .

Column 24,
Line 61, delete "polymemizable" and insert -- polymerizable --, therefor.

Signed and Sealed this

Tenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,841,190 B2
DATED : January 11, 2005
INVENTOR(S) : Liu, Junkang J.

It is certified that error appears in the above-identified patent and that said Letters Patent is hereby corrected as shown below:

Title page,
Item [56], References Cited, FOREIGN PATENT DOCUMENTS, delete "WO WO 9937720 7/1999".

Column 12,
Line 41, delete "(VI)" and insert (V) --, therefor.
Line 59, Delete "$F(CF(CF_3)CF_2O)_{25}CF2CF_3$" and insert -- $F(CF(CF_3)CF_2O)_{25}CF_2CF_3$ --, therefor.

Column 13,
Line 19, after "and" delete ",".

Column 17,
Table 1, (Notes) Note 3, delete "$F(CF(CF_3)CF_2O)_{25}CF2CF_3$" and insert -- $F(CF(CF_3)CF_2O)_{25}CF_2CF_3$ --, therefor.
Table 1, (Notes) Note 11, delete "propan" and insert -- propane --, therefor.

Column 19,
Line 14, delete "perfluoroployethers" and insert -- perfluoropolyethers --, therefor.

Column 23,
Line 65, delete "$Y-C_aF_{2a}O)_b-C_aF_{2a}-Y$" and insert -- $Y-(C_aF_{2a}O)_b-C_aF_{2a}-Y$ --, therefor.

Column 24,
Line 61, delete "polymemizable" and insert -- polymerizable --, therefor.

Signed and Sealed this

Thirty-first Day of May, 2005

JON W. DUDAS
*Director of the United States Patent and Trademark Office*